(12) United States Patent
Rantanen et al.

(10) Patent No.: US 12,611,113 B2
(45) Date of Patent: Apr. 28, 2026

(54) TECHNIQUES FOR IDENTIFYING REPRESENTATIVE PPG PULSES

(71) Applicant: Oura Health Oy, Oulu (FI)

(72) Inventors: Antti Aleksi Rantanen, Oulu (FI); Heli Tuulia Koskimäki, Oulu (FI); Juha Pärkkä, Oulu (FI); Shyamal Patel, San Francisco, CA (US); Olli Petteri Heikkinen, Oulu (FI); Tero Juhani Vallius, Kontio (FI); Jussi Petteri Järvelä, Kempele (FI); Mikka Petteri Kangas, Oulu (FI); Hannu Koivisto, Oulu (FI); Jukka Tapani Mäkinen, Oulu (FI); Pauli Juhani Ohukainen, Oulu (FI)

(73) Assignee: Oura Health Oy, Oulu (FI)

( * ) Notice: Subject to any disclaimer, the term of this patent is extended or adjusted under 35 U.S.C. 154(b) by 425 days.

(21) Appl. No.: 18/189,945

(22) Filed: Mar. 24, 2023

(65) Prior Publication Data

US 2024/0315582 A1 Sep. 26, 2024

(51) Int. Cl.
A61B 5/024 (2006.01)
A61B 5/00 (2006.01)
G16H 50/70 (2018.01)

(52) U.S. Cl.
CPC ........ A61B 5/02416 (2013.01); A61B 5/6826 (2013.01); G16H 50/70 (2018.01)

(58) Field of Classification Search
CPC .................................................. A61B 5/02416
See application file for complete search history.

(56) References Cited

U.S. PATENT DOCUMENTS

2014/0180136 A1* 6/2014 Su ...................... A61B 5/02416
600/479
2016/0360984 A1* 12/2016 Albadawi ............ A61B 5/7246
2023/0036114 A1* 2/2023 Whitehill ............. A61B 5/7221

OTHER PUBLICATIONS

"Multi-wavelength photoplethysmography method for skin arterial pulse extraction" by J. Liu et al. Biomed Optics Express. vol. 7, No. 10, 2016.*
"Study of a Ring-Type Surgical Pleth index Monitoring System Based on Flexible PPG Sensor" by C. Zhou et al. IEEE Sensors Jour. vol. 21, No. 13, 2021.*

* cited by examiner

*Primary Examiner* — Jason M Ip
(74) *Attorney, Agent, or Firm* — ArentFox Schiff LLP

(57) ABSTRACT

Methods, systems, and devices for identifying representative photoplethysmogram (PPG) pulses are described. A method may include acquiring a first set of PPG pulses from a user via a wearable device. The method may include comparing a set of morphological features of the first set of PPG pulses, and determining one or more PPG profiles for the user, where the one or more PPG profiles each include a set of morphological value ranges for the set of morphological features. The method may include acquiring a second set of PPG pulses from the user via the wearable device, and determining that one or more PPG pulses from the second set of PPG pulses match the one or more PPG profiles. The method may include determining one or more physiological metrics associated with the user based on the one or more PPG pulses matching the one or more PPG profiles.

18 Claims, 8 Drawing Sheets

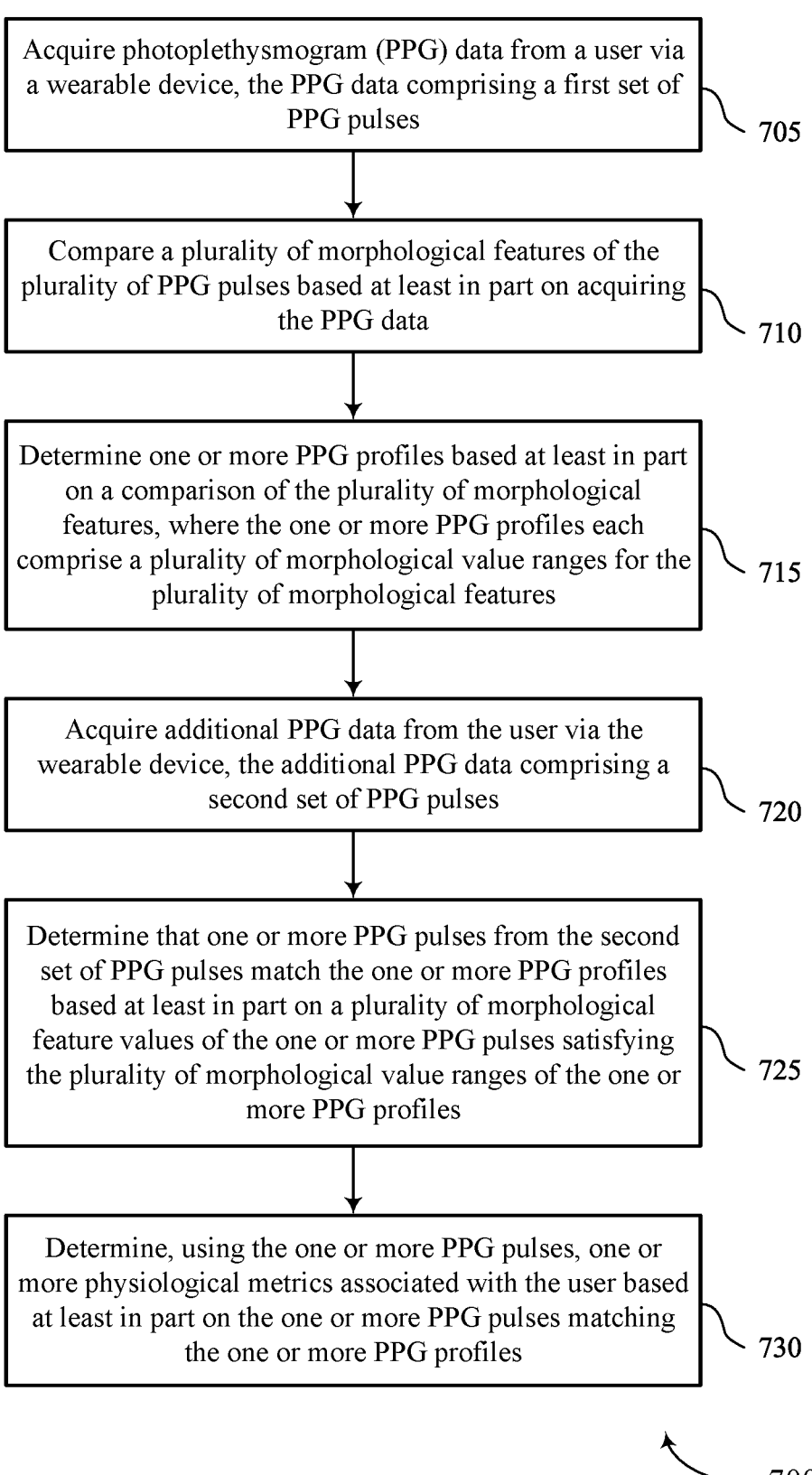

Acquire photoplethysmogram (PPG) data from a user via a wearable device, the PPG data comprising a first set of PPG pulses ⟍ 705

Compare a plurality of morphological features of the plurality of PPG pulses based at least in part on acquiring the PPG data ⟍ 710

Determine one or more PPG profiles based at least in part on a comparison of the plurality of morphological features, where the one or more PPG profiles each comprise a plurality of morphological value ranges for the plurality of morphological features ⟍ 715

Acquire additional PPG data from the user via the wearable device, the additional PPG data comprising a second set of PPG pulses ⟍ 720

Determine that one or more PPG pulses from the second set of PPG pulses match the one or more PPG profiles based at least in part on a plurality of morphological feature values of the one or more PPG pulses satisfying the plurality of morphological value ranges of the one or more PPG profiles ⟍ 725

Determine, using the one or more PPG pulses, one or more physiological metrics associated with the user based at least in part on the one or more PPG pulses matching the one or more PPG profiles ⟍ 730

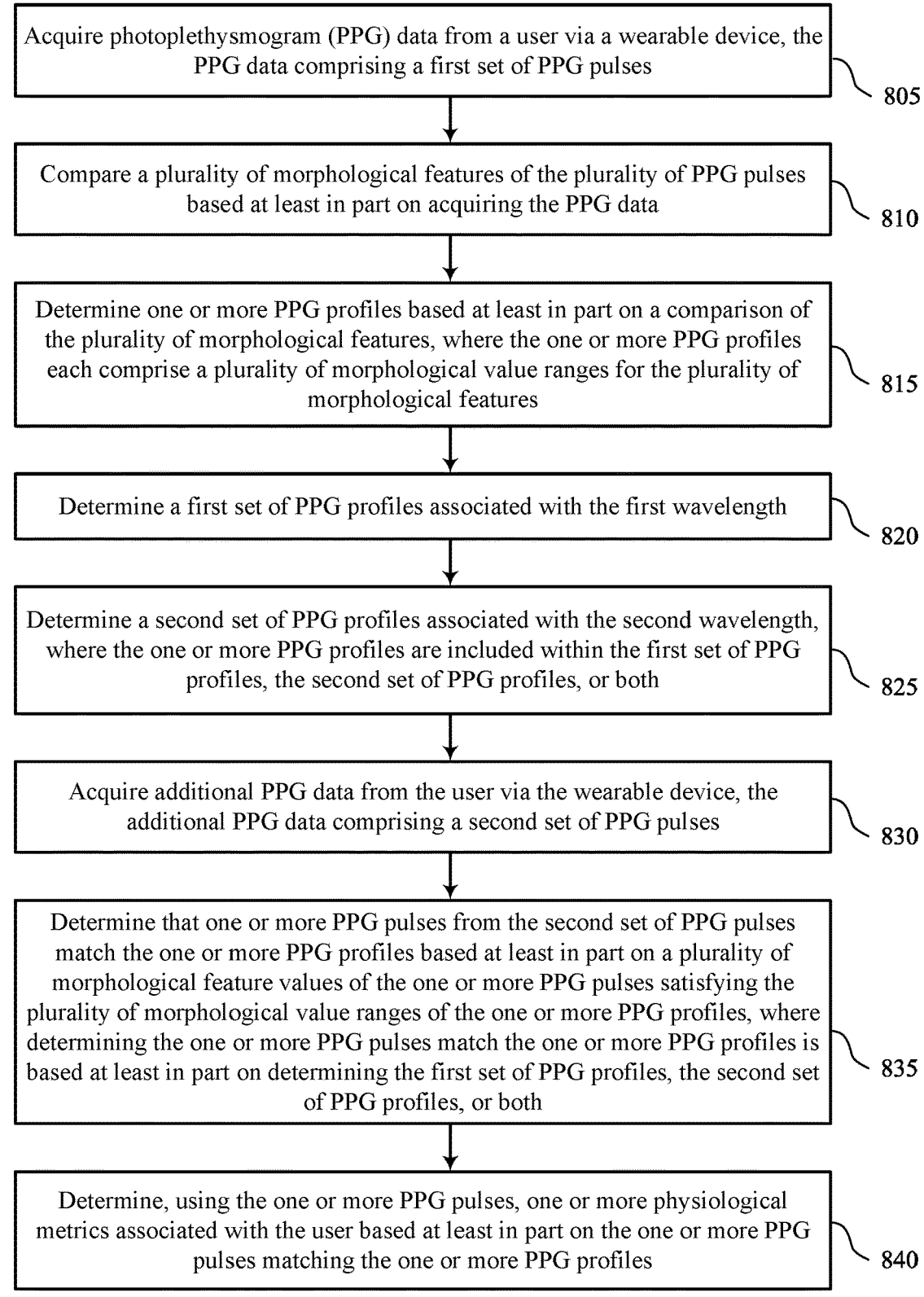

Acquire photoplethysmogram (PPG) data from a user via a wearable device, the PPG data comprising a first set of PPG pulses ⟍ 805

Compare a plurality of morphological features of the plurality of PPG pulses based at least in part on acquiring the PPG data ⟍ 810

Determine one or more PPG profiles based at least in part on a comparison of the plurality of morphological features, where the one or more PPG profiles each comprise a plurality of morphological value ranges for the plurality of morphological features ⟍ 815

Determine a first set of PPG profiles associated with the first wavelength ⟍ 820

Determine a second set of PPG profiles associated with the second wavelength, where the one or more PPG profiles are included within the first set of PPG profiles, the second set of PPG profiles, or both ⟍ 825

Acquire additional PPG data from the user via the wearable device, the additional PPG data comprising a second set of PPG pulses ⟍ 830

Determine that one or more PPG pulses from the second set of PPG pulses match the one or more PPG profiles based at least in part on a plurality of morphological feature values of the one or more PPG pulses satisfying the plurality of morphological value ranges of the one or more PPG profiles, where determining the one or more PPG pulses match the one or more PPG profiles is based at least in part on determining the first set of PPG profiles, the second set of PPG profiles, or both ⟍ 835

Determine, using the one or more PPG pulses, one or more physiological metrics associated with the user based at least in part on the one or more PPG pulses matching the one or more PPG profiles ⟍ 840

FIG. 8      ⟍ 800

TECHNIQUES FOR IDENTIFYING REPRESENTATIVE PPG PULSES

FIELD OF TECHNOLOGY

The following relates to wearable devices and data processing, including techniques for identifying representative photoplethysmogram (PPG) pulses.

BACKGROUND

Some wearable devices (e.g., wearable rings, wearable watches or bracelets, or the like) may be configured to collect photoplethysmogram (PPG) data from users. In some examples, the PPG data may indicate physiological metrics (e.g., measurements) for a user, such as metrics related to cardiac output (e.g., heart rate, heart rate variability (HRV), blood pressure, oxygen levels (e.g., SpO2), or the like. However, some of the PPG pulses used to measure a specific physiological feature may vary in morphology (e.g., magnitude of pulses, timing of pulses, shape of pulses) and some of the PPG pulses may inaccurately represent a physiological measurement of the user. In some implementations, a system that uses the inaccurate PPG pulses or fails to consider additional factors that affect the PPG data may output unreliable physiological metrics of the user.

BRIEF DESCRIPTION OF THE DRAWINGS

FIGS. 7 and 8 illustrate flowcharts showing methods that support techniques for identifying representative PPG pulses in accordance with aspects of the present disclosure.

DETAILED DESCRIPTION

Figure 1:
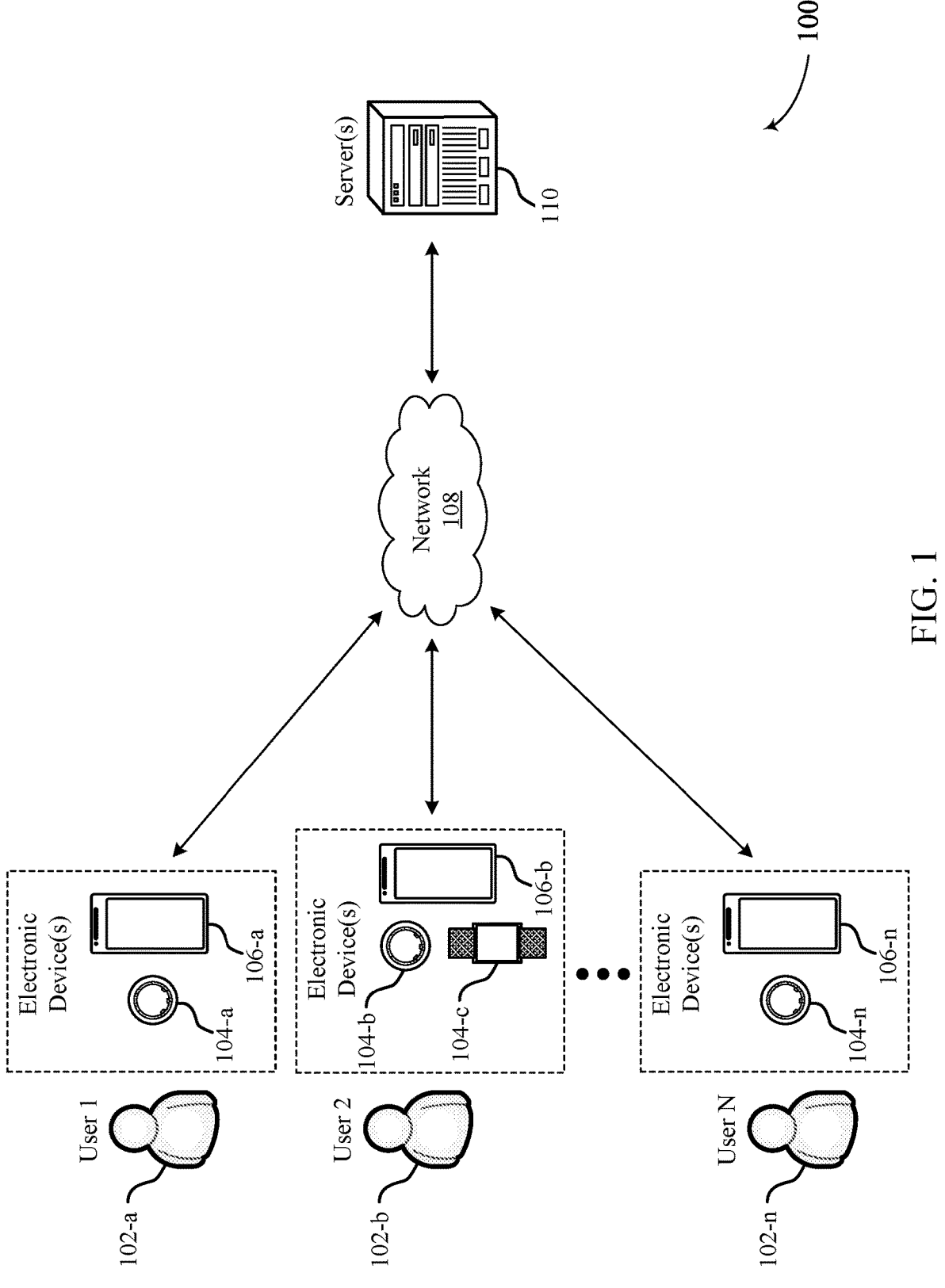
FIG. 1 illustrates an example of a system that supports techniques for identifying representative photoplethysmogram (PPG) pulses in accordance with aspects of the present disclosure.

Some wearable devices may be configured to utilize light to acquire photoplethysmogram (PPG) data from users via wearable devices (e.g., wearable ring devices, watches or bracelets, or the like). In some examples, the PPG data may indicate physiological metrics (e.g., measurements, parameters) of a user, such as a heart rate metric, a heart rate variability (HRV) metric, a blood oxygen saturation metric, a blood pressure metric, an arterial reactivity metric, or the like. In some implementations, a wearable device may collect the PPG data in the form of one or more sets of PPG pulses to measure specific physiological parameters of the user.

However, not all PPG pulses may exhibit the same morphological features or characteristics. In other words, PPG pulses may exhibit varying shapes and characteristics. That is, morphological features of PPG pulses (e.g., PPG pulse amplitude, duration, slope, curvature, relationships between peaks) may vary from one PPG pulse to the next, and some of the PPG pulses may inaccurately represent a physiological measurement. Additionally, or alternatively, factors such as light, pressure, a posture of the user (e.g., the user is sitting or standing), or a hydration of the user (e.g., the user may have swollen fingers due to lack of hydration) may affect the accuracy of the PPG data. In particular, a system that uses the inaccurate PPG pulses or fails to account for additional factors that affect the PPG data may result in unreliable physiological measurements. That is, multiple systems may benefit from one or more techniques for identifying PPG pulses that accurately represent the physiological metrics of one or more users.

As described herein, a system may use one or more techniques to identify one or more representative (e.g., common, average) PPG pulses that accurately represent the physiological metrics of the user. That is, the one or more techniques may be used to identify the PPG pulses that are of high quality and accurately reflect physiological metrics of the user. To identify the one or more PPG pulses that accurately represent the physiological metrics of the user, the wearable device may acquire PPG data that includes a first set of PPG pulses from the user. In some aspects, the system may compare multiple morphological features from the first set of PPG pulses for each specific physiological measurement. Further, the system may determine one or more PPG profiles (e.g., one or more representative PPG pulses, one or more common pulse templates) for each specific physiological metric based on the comparison of the multiple morphological features of the first set of PPG pulses. That is, each of the one or more PPG profiles may include a set of multiple morphological value ranges for the multiple morphological features. In some examples, each of the PPG profiles may represent a representative (e.g., common, average) pulse calculated from the first set of PPG pulses for each specific physiological measurement.

In addition, the system may acquire additional PPG data from the user via the wearable device. In some cases, the system may acquire the additional PPG data from the user as a second set of PPG pulses. In some implementations, the system may determine that one or more PPG pulses from the second set of PPG pulses match the one or more PPG profiles from the first set of PPG pulses. That is, the system may detect that multiple morphological feature values of the second set of PPG pulses satisfy the multiple morphological value ranges of the one or more PPG profiles. In other words, the system may identify which PPG pulses of the second set of PPG pulses "match" the PPG profiles.

Subsequently, the system may determine one or more physiological metrics associated with the user based on the one or more PPG pulses from the second set of PPG pulses matching the one or more PPG profiles from the first set of PPG pulses. Stated differently, the system may utilize the PPG pulses that "match" the PPG profiles (e.g., the system may utilize "representative" PPG pulses) to perform physiological measurements for the user. Alternatively, the system may detect that the one or more PPG pulses from the second set of PPG pulses fails to match the one or more PPG profiles from the second set of PPG pulses and may refrain from using that specific physiological metric associated with the user or otherwise take this information into account.

In some aspects, the wearable device may identify the one or more representative PPG pulses for each user using the existing hardware features of the wearable device. In some examples, the system may define the one or more PPG pulse profiles (e.g., one or more PPG templates) that represent common PPG pulses of the user. That is, the system may acquire one or more PPG pulses and may compare each of the PPG pulses to each other to determine the one or more PPG pulse profiles. In such cases, the system may determine the one or more PPG profiles by identifying common (e.g., average) values (e.g., average length, amplitude, slope, or the like) of the multiple PPG pulses. For example, the system may define one or more PPG pulse profiles based on common PPG pulses acquired from the user via a day-time calibration sequence. That is, the calibration sequence may be initiated to define valid samples to determine which of the PPG pulses are suitable (e.g., reliable) for performing physiological measurements. In some cases, the system may utilize a changing correlation between different signal paths to find an optimal measurement time for the PPG pulses.

In some implementations, the system may account for posture estimation of the user, and may determine different sets of PPG profiles based on different postures of the user. For example, the system may detect the posture of the user (e.g., the user may be standing, sitting, lying down, or the like) which may affect the signal quality metrics of the PPG pulses. As such, the system may use the PPG pulse profiles, the calibration sequence, and additional factors to select accurate PPG pulses with appropriate signal quality metrics that represent the physiological metrics of the user (e.g., first set of PPG profiles for when the user is standing, and second set of PPG profiles for when the user is sitting).

Aspects of the disclosure are initially described in the context of systems supporting physiological data collection from users via wearable devices. Aspects of the disclosure are further illustrated by and described with reference to apparatus diagrams, system diagrams, and flowcharts that relate to techniques for identifying representative PPG pulses.

FIG. 1 illustrates an example of a system 100 that supports techniques for identifying representative PPG pulses in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, HRV, actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight." or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for identifying one or more representative (e.g., common, average) PPG pulses that accurately represents the physiological metrics (e.g., measurements, parameters) of the user. By identifying "representative" PPG pulses, techniques described herein may enable wearable devices to select PPG pulses that will result in high-quality measurements (e.g., physiological metrics). In some examples, the physiological metrics of a user that may be determined using PPG pulses may include a heart rate metric, an HRV metric, a blood oxygen saturation metric, a blood pressure metric, an arterial reactivity metric, or the like.

To identify the one or more PPG pulses that accurately represent the physiological metrics of the user, the wearable device 104 may acquire PPG data that includes a first set of PPG pulses from the user 102. In some aspects, the system 100 may compare multiple morphological features from the first set of PPG pulses. For instance, the system 100 may compare morphological features such as amplitudes of PPG pulses, time durations of a set of PPG pulses, slopes (e.g., first derivatives) of a set of PPG pulses, curvatures (e.g., second derivatives) of a set of PPG pulses, relationships between peaks (e.g., systolic versus diastolic) of PPG pulses, or the like. Further, the system 100 may determine one or more PPG profiles (e.g., one or more representative PPG pulses, one or more common pulse templates) for the specific physiological metric based on the comparison of the multiple morphological features of the first set of PPG pulses. That is, each of the one or more PPG profiles may include a set of multiple morphological value ranges for the multiple morphological features. In some examples, each of the PPG profiles may represent a representative (e.g., common, average) pulse calculated from the first set of PPG pulses for the specific physiological measurement.

In addition, the system 100 may acquire additional PPG data from the user 102 via the wearable device 104. In some cases, the system 100 may acquire the additional PPG data from the user 102 as a second set of PPG pulses. In some implementations, the system 100 may determine that one or more PPG pulses from the second set of PPG pulses match the one or more PPG profiles from the first set of PPG pulses. That is, the system 100 may detect that multiple morphological feature values of the second set of PPG pulses satisfy the multiple morphological value ranges of the one or more PPG profiles. Stated differently, the system 100 may identify PPG pulses that match the respective PPG profiles.

Subsequently, the system 100 may determine one or more physiological metrics associated with the user based on the one or more PPG pulses from the second set of PPG pulses matching the one or more PPG profiles from the first set of PPG pulses. In other words, the system 100 may utilize the PPG pulses that match the respective PPG profiles to perform physiological measurements for the user (e.g., perform heartrate measurements, HRV measurements, SpO2 measurements, and the like). Alternatively, the system 100 may detect that the one or more PPG pulses from the second set of PPG pulses fails to match the one or more PPG profiles from the second set of PPG pulses and may refrain from using that physiological metric associated with the user.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
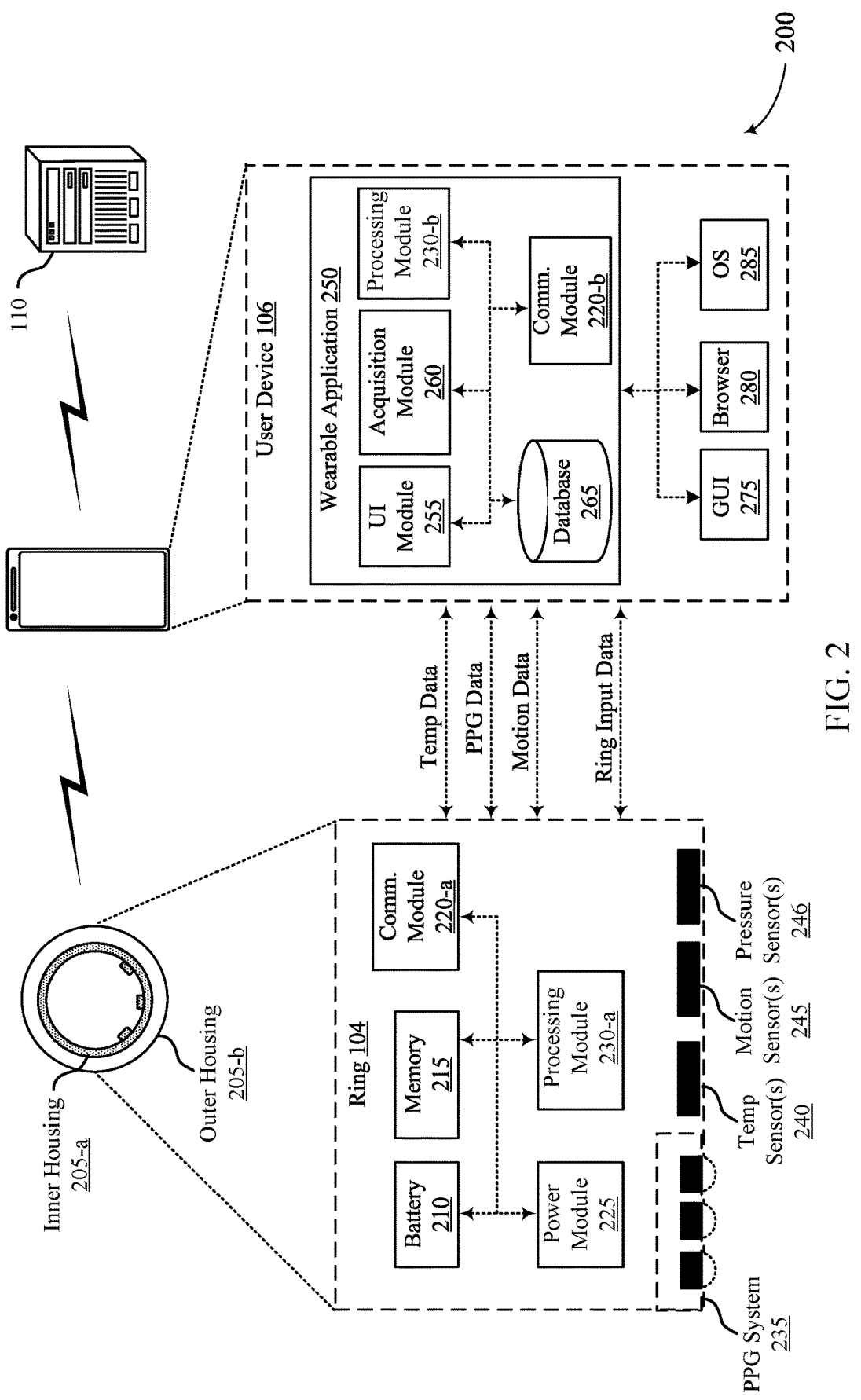
FIG. 2 illustrates an example of a system that supports techniques for identifying representative PPG pulses in accordance with aspects of the present disclosure.

FIG. 2 illustrates an example of a system 200 that supports techniques for identifying representative PPG pulses in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a,* a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits).

The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-a herein. In some implementations, the processing module 230-a (e.g., a microcontroller) may include additional features associated with other modules, such as communication functionality provided by the communication module 220-a (e.g., an integrated Bluetooth Low Energy transceiver) and/or additional onboard memory 215.

The communication module 220-a may include circuits that provide wireless and/or wired communication with the user device 106 (e.g., communication module 220-b of the user device 106). In some implementations, the communication modules 220-a, 220-b may include wireless communication circuits, such as Bluetooth circuits and/or Wi-Fi circuits. In some implementations, the communication modules 220-a, 220-b can include wired communication circuits, such as Universal Serial Bus (USB) communication circuits. Using the communication module 220-a, the ring 104 and the user device 106 may be configured to communicate with each other. The processing module 230-a of the ring may be configured to transmit/receive data to/from the user device 106 via the communication module 220-a. Example data may include, but is not limited to, motion data, temperature data, pulse waveforms, heart rate data, HRV data, PPG data, and status updates (e.g., charging status, battery charge level, and/or ring 104 configuration settings). The processing module 230-a of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep day's may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the respective devices of the system 200 may support techniques for identifying representative PPG pulses of a user 102 collected via a wearable device 104 (e.g., a wearable ring device). To identify the one or more PPG pulses that accurately represent one or more physiological metrics of user 102, the wearable device 104 may acquire PPG data that includes a first set of PPG pulses from the user 102. In some examples, the wearable device 104 may collect PPG data based on an arterial blood flow, a capillary arterial flow, and/or a venous blood flow of the user 102 via a PPG system 235. That is, the PPG system 235 may utilize one or more light sources (e.g., LEDs) and photodetectors near the surface of the skin to measure the volumetric variations of blood flow of the user 102. In some examples, a triple LED (e.g., red, green, and IR) PPG system 235 may enable the wearable device 104 to propagate multiple light waves and measure multiple wavelengths. In some examples, the PPG data indicates physiological metrics for each respective user 102. For example, the wearable device 104 may collect PPG data indicating physiological metrics, such as a heart rate metric, an HRV metric, a blood oxygen saturation metric, a blood pressure metric, an arterial reactivity metric (e.g., a cardiovascular age), or the like.

In some examples, the system 200 may compare morphological features from the first set of PPG pulses measured from the wearable device 104. For example, the system 200 may compare the morphological features of the first set of PPG pulses such as the amplitudes of PPG pulses, time durations of PPG pulses, slopes of PPG pulses, curvatures of PPG pulses, relationships of PPG pulses, or the like. Further, the system 200 may compare the morphological features from the first set of PPG pulses to determine multiple morphological value ranges that for each of the morphological features (e.g., the system 200 determines values of W, X, Y, and Z, so that the system can determine that one or more PPG pulses with an amplitude between X and Y and a time duration between W and Z satisfies a respective PPG profile). In some examples, the morphological value ranges include a range of average morphological values for each morphological feature, a range of median morphological values for each morphological feature, and a range of mode morphological values for each morphological features, or a combination of ranges (e.g., the system 200 determines the average amplitude of PPG pulses in addition to a range of amplitudes that may match one or more PPG profiles).

Upon determining the morphological value ranges of the first set of PPG pulses, the system 200 may determine one or more PPG profiles (e.g., one or more representative PPG pulses, one or more common pulse templates) for the user 102. In some examples, each of the PPG profiles may represent the morphological value ranges and may represent physiological features of the user 102. For example, a PPG profile may include a "representative" or average morphological features within the determined morphological ranges, such as an amplitude (e.g., size) within a range (e.g., values between X and Y) for a duration in time (e.g., a time between W and Z). As such, each of the PPG profiles may represent a normal (e.g., common, average) PPG pulse calculated from the morphological value ranges from first set of PPG pulses for a specific physiological measurement.

In some implementations, the system 200 may determine PPG profiles based on one or more wavelengths of light. That is, the system 200 may generate multiple sets of PPG profiles for multiple wavelengths (e.g., a first set of PPG profiles for green light, a second set of PPG profiles for red light, a third set of PPG profiles for IR light). In some examples, the PPG system 235 may acquire PPG data using a first light associated with a first wavelength. The PPG system 235 may compare multiple PPG pulses of the PPG data acquired with a first wavelength and may compare the one or more morphological features. That is, the PPG system 235 may determine a first set of PPG profiles associated with the first wavelength based on the comparison of multiple PPG pulses using the first light. In addition, the PPG system 235 may acquire PPG data using a second light associated with a second wavelength. The PPG system 235 may compare multiple PPG pulses for the PPG data found using a second wavelength and may compare the one or more morphological features. As such, the PPG system 235 may determine a second set of PPG profiles associated with the second wavelength. In such cases, the system 200 may be configured to compare subsequently-acquired PPG pulses with the respective PPG profiles in order to identify representative PPG pulses associated with the respective wavelengths (e.g., compare PPG pulses collected via the first wavelength to the first set of PPG profiles, compare PPG pulses collected via the second wavelength to the second set of PPG profiles).

In some aspects, the system 200 may generate the one or more PPG profiles based on physiological (e.g., PPG) data and additional sensor measurements that indicate that the user 102 is in a specific posture (e.g., user 102 is sitting, standing, lying down, or the like). In particular, PPG pulses collected while the user is in different postures may exhibit different morphological features (e.g., different shapes, amplitudes, durations, etc.). As such, the system 200 may be configured to generate different sets of PPG profiles based on the different postures of the user (e.g., first set of PPG profiles for a standing posture, second set of PPG profiles for a sitting posture).

The wearable device 104 may include one or more sensors that are able to measure or estimate the posture of the user 102, including one or more motion sensors 245, such as accelerometers (e.g., motion/activity sensors), and the one or more gyro sensors. In some examples, the one or more motion sensors 245 and the one or more gyro sensors may measure a direction of movement and orientation changes of a user to help determine the position/posture of the user 102. Additionally, or alternatively, a pressure sensor 246 of the ring 104 may measure the ambient air pressure with respect to a relative pressure to the user 102 (e.g., about elevation of the hand of the user 102, about the air pressure acting on the point of measurement against a tissue of the user 102, such as internal hydrostatic pressure) to determine the position of the user 102. In some examples, the pressure sensor 246 may measure hydrostatic pressure acting against one or more vein walls inside of the user 102 that may affect the PPG pulse morphology of PPG pulses. Moreover, in some cases, the system 200 may utilize one or more other data sources (such as additional wearable devices) to determine a posture of the user.

In some examples, the system 200 may acquire PPG data corresponding to different posture states of the user 102. For example, the system 200 may acquire PPG data for a first time interval where the user 102 is in a sitting posture (e.g., a first posture) and determine a first set of PPG profiles associated with the sitting posture. In addition, the system 200 may acquire physiological data for a second time interval where the user 102 is in a standing posture (e.g., a second posture) and determine a second set of PPG profiles associated with the standing posture. As such, the system 200 may detect that the user 102 is positioned in a sitting posture because the PPG data corresponds to the first set of PPG profiles that are associated with the sitting posture. Further, the system 200 may generate multiple PPG profiles over periods of time that accurately represent PPG pulses associated with respective postures of the user 102.

In some examples, the system 200 may determine one or more PPG profiles based on common PPG pulses collected from the user 102 via a day-time calibration sequence. The day-time calibration sequence may define valid samples and determine the PPG pulses suitable for performing measurements. In some cases, the system 200 may utilize a changing correlation between different signal paths to find an optimal measurement time for the PPG pulses. That is, the system 200 may dynamically select one or more signal paths that produce reliable PPG pulses. As such, the system 200 may use appropriate signal paths, the calibration sequence, and additional factors to select representative PPG pulses with appropriate signal quality metrics for the one or more PPG profiles.

In some aspects, the system 200 may initiate a measurement calibration sequence by instructing the user (e.g., via the wearable application 250 of a user device 106) to position themselves in a series of different postures like standing up, sitting, and lying down (e.g., similar to how traditional blood pressure measurement with an arm cuff is performed while the user is sitting down with their arm laying flat on a surface such as a table). In such cases, sensor calibration may be performed with these predetermined postures when the device is deployed. Moreover, recalibration may be performed at regular or irregular time intervals.

Additionally, or alternatively, the system 200 may determine one or more PPG profiles based on relative pressure between the wearable device 104 and the user 102. Varying pressures between the wearable device 104 and the tissue of the user may cause morphological features of acquired PPG pulses to change. As such, the system 200 may be configured to determine different sets of PPG profiles associated with different pressure ranges. In particular, with enough applied pressure, blood flow can be cut off completely from top layers of tissue. This may be illustrated by PPG signals acquired using green light disappearing earlier (e.g., becoming undetectable) as compared to other PPG signals collected using IR light as increasing pressure is applied, as IR light penetrates to deeper layers of tissue and is able to collect PPG data even when blood flow is cut off from higher layers of tissue. As the external sensor pressure acts against body internal pressure, a correlation to blood pressure may be determined, and it may be possible to determine at least one sensor pressure reference point at the pressure when the green PPG pulse shape is not visible due to applied pressure.

In some examples, the wearable device 104 may be equipped with the pressure sensor 246 that measures contact pressure between the wearable device 104 and the user 102. In some aspects, the system 200 may acquire PPG data indicating that additional pressure is applied between the wearable device 104 and a tissue of the user 102. In some examples, additional pressure is applied when the user 102 grabs an object, the user 102 has swollen extremities (e.g., fingers) due to dehydration, or the like. In some examples, the wearable device 104 may measure pressure via optical, piezoresistive, capacitive, or other pressure-sensing techniques. In some examples, the pressure sensor 246 may include one or more piezoelectric sensors. In other implementations, the system 200 may enable the wearable device 104 to use bioimpedance techniques to measure the response of an external current via the wearable device 104. That is, the wearable device 104 may use the bioimpedance techniques to measure electrodermal activity and quantify the contact pressure (e.g., quality) between the wearable device 104 and the skin of the user 102. In some examples, the wearable device 104 may include a blood pressure cuff to acquire additional physiological metrics from the user 102.

To account for different pressures that may affect the morphological features of the PPG pulses, the system 200 may determine the multiple PPG profiles based on different values of pressure between the wearable device 104 and the user 102. In some cases, the system 200 may acquire physiological data associated with different pressure states between the user 102 and the wearable device 104. For example, the system 200 may acquire the physiological data via the pressure sensor 246 for a first time interval where the user 102 is in a normal pressure state (e.g., a first pressure state where the hand position of the user 102 is unclenched or the user 102 is hydrated and fingers are unswollen) and determine a first set of PPG profiles associated to the normal pressure state. In addition, the system 200 may acquire the physiological data via the pressure sensor 246 for a second time interval where the user 102 may apply additional pressure to the wearable device 104 (e.g., by gripping a handle or other object with varying grip strength). That is, the system 200 may detect an additional pressure state (e.g., a second pressure state where the hand position of the user 102 is clenched or the user 102 is dehydrated and fingers are swollen) and determine a second set of PPG profiles associated with the additional pressure state. In some aspects, the system 200 may determine multiple PPG profiles that correspond to different pressure states between the user 102 and the wearable device 104. That is, the system 200 may apply the multiple PPG profiles to determine whether additional PPG data accurately represents physiological metrics of the user 102 when under specific pressure states. For example, the system 200 may compare PPG pulses collected under a first pressure state to the first set of PPG pulses, and may compare PPG pulses collected under a second pressure state to the second set of PPG pulses.

Additionally, or alternatively, the wearable device 104 may utilize the pressure sensor 246 for contact pressure estimation in combination with the PPG system 235 to accurately measure the physiological parameters of the user 102. In some examples, the PPG system 235 may account for a skin color (e.g., light to dark skin color) measurement. For example, the PPG system 235 may enable the wearable device 104 to measure further penetration depths for a user with lighter skin color compared to a user with a darker skin color. In some examples, the wearable device 104 may use the PPG system 235 to measure PPG measurements via reflective techniques. For example, the wearable device 104 may use a lock in amplifier (LIA) to enable light to be transmitted through the tissue of the user and may measure PPG measurements (e.g., transmittal PPG measurements) based on the light that is transmitted through the tissue. In some implementations, the system 200 may determine a correlation between different wavelengths collected via the PPG system 235 for an optical path.

In addition, the system 200 may enable the wearable device 104 to acquire additional PPG data that includes a second set of PPG pulses from the user 102 via the PPG system 235. In some examples, the system 200 may instruct the wearable device 104 to send the second set of PPG pulses to a user device 106, and the user device 106 may compare morphological features between the second set of PPG pulses and the one or more PPG profiles from the first set of PPG pulses. In some examples, the user device 106 may determine that one or more PPG pulses from the second set of PPG pulses match the one or more PPG profiles from the first set of PPG pulses. That is, the system 200 may use the database 265 of the wearable application 250 to determine if the second set of PPG pulses satisfy the multiple morphological value ranges of the one or more PPG profiles from the first set of PPG pulses stored in the database 265. In other words, the system 200 may check if the one or more PPG pulses from the second set of PPG values may be in the range of the morphological values displayed from the representative PPG pulse generated from the first set of PPG values. As such, the system 200 may determine whether the one or more representative PPG pulses represent accurate, reliable physiological metrics for the user 102 based on using the second set of PPG pulses and may compare whether the second set of PPG pulses match the one or more PPG profiles from the first set of PPG pulses.

Figure 3:
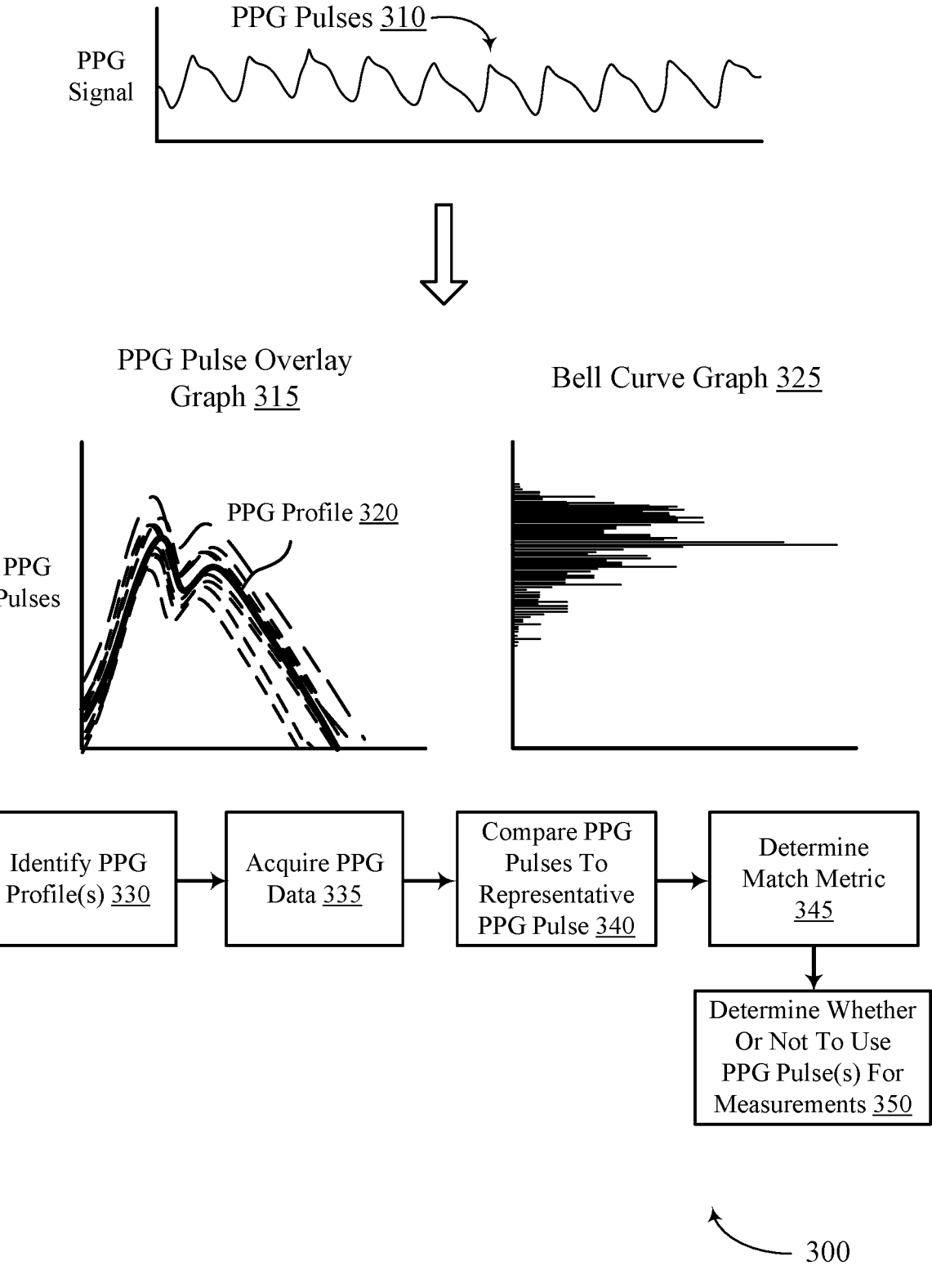
FIG. 3 illustrates an example of a system that supports techniques for identifying representative PPG pulses in accordance with aspects of the present disclosure.

FIG. 3 illustrates an example of a system 300 that supports techniques for identifying representative PPG pulses in accordance with aspects of the present disclosure. In some implementations, the system 300 may implement, or be implemented by, aspects of the system 100 and the system 200 as described with reference to FIGS. 1 and 2. For example, the system 300 may be implemented by a wearable device 104 (e.g., a ring 104), a user device 106, one or more servers 110, or any combination thereof. In the following description of the system 300, the operations may be performed in a different order than the example order shown, or the operations may be performed in different orders or at different times. Some operations may also be omitted from the system 300, and other operations may be added to the system 300.

In the example of FIG. 3, the system 300 may acquire PPG data from a user via a wearable device 104. In particular, FIG. 3 illustrates a PPG graph 305 that illustrates a PPG signal with a set of multiple PPG pulses 310 (e.g., a first set of PPG pulses). In some aspects, the PPG signal with an associated signal quality metric may represent or be used to determine a physiological metric associated with the user, such as a heart rate metric, an HRV metric, a blood oxygen saturation metric, a blood pressure metric, an arterial reactivity metric, or the like. In the PPG graph 305, the wearable device 104 may use the PPG signal to acquire PPG data in the form of multiple PPG pulses 310. In some aspects, each of the PPG pulses 310 may be associated with respective morphological features that may include or describe features of the PPG pulses 310. For example, morphological features of a PPG pulse 310 may include certain features or characteristics of the respective PPG pulse 310, such as an amplitude of the PPG pulse 310, time duration of the PPG pulse 310, a slope of the PPG pulse 310 (e.g., first derivative), a curvature of the PPG pulse 310 (e.g., second derivative), relationships between the PPG pulse 310 and adjacent PPG pulses 310, or the like.

Additionally, the system 300 may compare each of the morphological features of the PPG pulses 310 to determine multiple morphological value ranges for each of the morphological features (e.g., value ranges for PPG pulse 310 amplitudes, time durations, curvatures, etc.). In some examples, the system 300 may compare morphological features graphically to illustrate the morphological value ranges.

For example, in FIG. 3, the system 300 may compare one or more morphological value ranges of PPG pulses 310 with a PPG pulse overlay graph 315 or a bell curve graph 325. That is, the system 300 may use one or both graphs to compare each of the PPG pulses 310 and check where the morphological value ranges overlap in order to determine a representative PPG pulse 320 (e.g., a normal PPG pulse, a template PPG pulse) that exhibits the common or average values of the PPG pulses 310 (e.g., common/average amplitude, common/average slope, etc.).

For instance, by overlaying the respective PPG pulses 310 with one another via the PPG pulse overlay graph 315, the system 300 may be configured to identify the average or most common features (e.g., average amplitude, slope, curvature, time duration, etc.) across the PPG pulses 310, which may be used to identify "representative" PPG pulses (e.g., PPG profiles 320). Similarly, the system 300 may calculate a morphological feature value for each of the PPG pulses 310 (e.g., amplitude of each PPG pulse, slope of each PPG pulse, etc.), and generate the bell curve graph 325 illustrating the determined morphological feature values for the set of PPG pulses 310. In this example, the bell curve graph 325 may be used to determine the average, median, or most common morphological feature value, which may be used to identify "representative" PPG pulses (e.g., PPG profiles 320).

In some implementations, the system 300 may identify representative PPG pulses (e.g., PPG profiles, or PPG templates). In the example of FIG. 3, at 330, the system 300 may identify the PPG profiles 320 (e.g., representative PPG pulses 310) to use to compare additional PPG data from the user. In some examples, the term "PPG profiles 320" may be used interchangeably to the terms "representative PPG pulses", "PPG templates," and the like, as described herein. In other words, at 330, the system 300 may identify one or more PPG profiles 320 that exhibit average or common morphological values. As described previously herein, the system 300 may be configured to identify different sets of PPG profiles 330, such as different sets of PPG profiles 320 for different wavelength ranges, different sets of PPG profiles 320 for different user postures and/or pressures, different sets of PPG profiles 320 for different types of measurements, and the like.

At 335, the wearable device 104 of the system 300 may acquire additional PPG data, such as one or more PPG pulses, from the user. In some examples, the system 300 may acquire additional PPG data at different time intervals (e.g., time periods) throughout a day (e.g., morning, noon, night). In some aspects, the additional PPG data may be acquired via PPG systems using one or more light wavelengths from one or more LEDs.

At 340, the system 300 (e.g., wearable device 104, user device 106, servers 110) may compare the one or more PPG pulses from the additional PPG data collected at 335 to the PPG profiles 320 determined at 330. That is, the system 300 may determine which PPG pulses collected at 335 match the one or more PPG profiles 320. In some cases, the system 300 may be configured to identify a set of consecutive PPG pulses from the additional PPG data that match the PPG profile(s) 320.

In some examples, when performing the comparison at 340, the system 300 may account for factors such as the posture of the user, pressure states between the user and the wearable device, wavelength of light used to collect the additional PPG data at 335, and the like. For example, in cases where the additional PPG data acquired at 335 is collected using green light, the system 300 may compare the PPG pulses to one or more PPG profiles 320 associated with green light. By way of another example, in cases where the additional PPG data is acquired at 335 during a time that the user is in a standing posture, the system 300 may compare the PPG pulses to one or more PPG profiles 320 associated with a standing posture.

At 345, the system 300 may identify one or more PPG pulses acquired at 335 that match the one or more PPG profiles 320. For example, the system 300 may determine that a set of consecutive PPG pulses from the additional PPG data match the PPG profiles 320. That is, the system 300 may determine that the additional PPG pulses exhibit morphological feature values that fall within the morphological feature value ranges of the PPG profiles 320.

At 350, the system 300 may determine whether or not to use the additional PPG pulses for physiological measurements. In particular, the system 300 may determine whether or not to use PPG pulses for physiological measurements based on whether or not the respective PPG pulses match the one or more PPG profiles. In some examples, the system 300 may determine that the additional PPG pulses satisfy the morphological value ranges of the representative PPG pulse 320, and may therefore use the one or more additional PPG pulses to perform physiological measurements for the user (e.g., use the PPG pulses to determine physiological metrics such as heart rate, HRV, etc.). Alternatively, the system 300 may identify one or more additional PPG pulses that fail to match the PPG profiles 320, and may therefore refrain from using such PPG pulses to perform physiological measurements.

Figure 4:
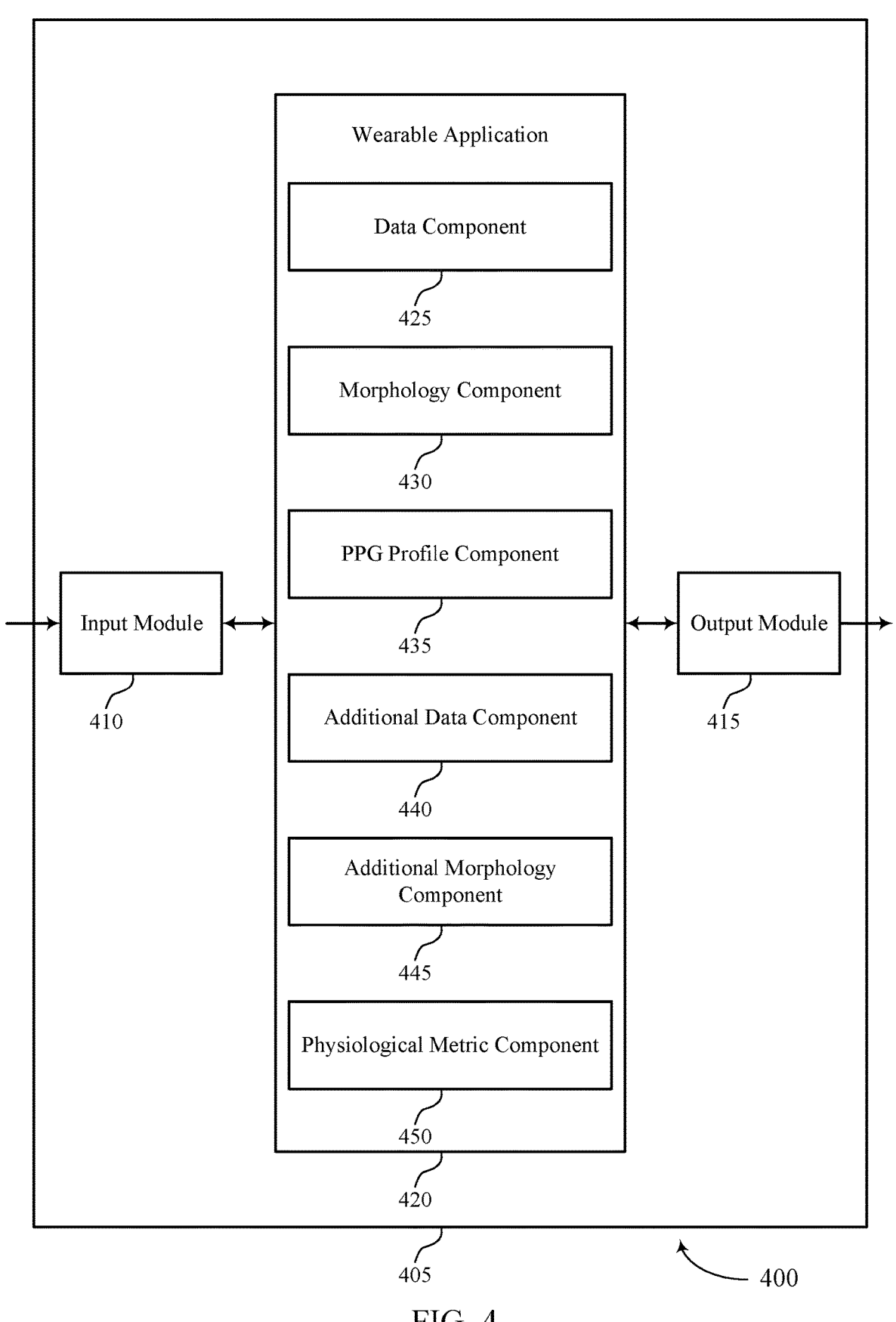
FIG. 4 illustrates a block diagram of an apparatus that supports techniques for identifying representative PPG pulses in accordance with aspects of the present disclosure.

FIG. 4 illustrates a block diagram 400 of a device 405 that supports techniques for identifying representative PPG pulses in accordance with aspects of the present disclosure. The device 405 may include an input module 410, an output module 415, and a wearable application 420. The device 405 may also include a processor. Each of these components may be in communication with one another (e.g., via one or more buses).

The input module 410 may provide a means for receiving information such as packets, user data, control information, or any combination thereof associated with various information channels (e.g., control channels, data channels, information channels related to illness detection techniques). Information may be passed on to other components of the device 405. The input module 410 may utilize a single antenna or a set of multiple antennas.

The output module 415 may provide a means for transmitting signals generated by other components of the device 405. For example, the output module 415 may transmit information such as packets, user data, control information, or any combination thereof associated with various information channels (e.g., control channels, data channels, information channels related to illness detection techniques). In some examples, the output module 415 may be co-located with the input module 410 in a transceiver module. The output module 415 may utilize a single antenna or a set of multiple antennas.

For example, the wearable application 420 may include a data component 425, a morphology component 430, a PPG profile component 435, an additional data component 440, an additional morphology component 445, a physiological metric component 450, or any combination thereof. In some examples, the wearable application 420, or various components thereof, may be configured to perform various operations (e.g., receiving, monitoring, transmitting) using or otherwise in cooperation with the input module 410, the output module 415, or both. For example, the wearable application 420 may receive information from the input module 410, send information to the output module 415, or be integrated in combination with the input module 410, the output module 415, or both to receive information, transmit information, or perform various other operations as described herein.

The data component 425 may be configured as or otherwise support a means for acquiring PPG data from a user via a wearable device, the PPG data comprising a first set of PPG pulses. The morphology component 430 may be configured as or otherwise support a means for comparing a plurality of morphological features of the plurality of PPG pulses based at least in part on acquiring the PPG data. The PPG profile component 435 may be configured as or otherwise support a means for determining one or more PPG profiles based at least in part on a comparison of the plurality of morphological features, wherein the one or more PPG profiles each comprise a plurality of morphological value ranges for the plurality of morphological features. The additional data component 440 may be configured as or otherwise support a means for acquiring additional PPG data from the user via the wearable device, the additional PPG data comprising a second set of PPG pulses. The additional morphology component 445 may be configured as or otherwise support a means for determining that one or more PPG pulses from the second set of PPG pulses match the one or more PPG profiles based at least in part on a plurality of morphological feature values of the one or more PPG pulses satisfying the plurality of morphological value ranges of the one or more PPG profiles. The physiological metric component 450 may be configured as or otherwise support a means for determining, using the one or more PPG pulses, one or more physiological metrics associated with the user based at least in part on the one or more PPG pulses matching the one or more PPG profiles.

Figure 5:
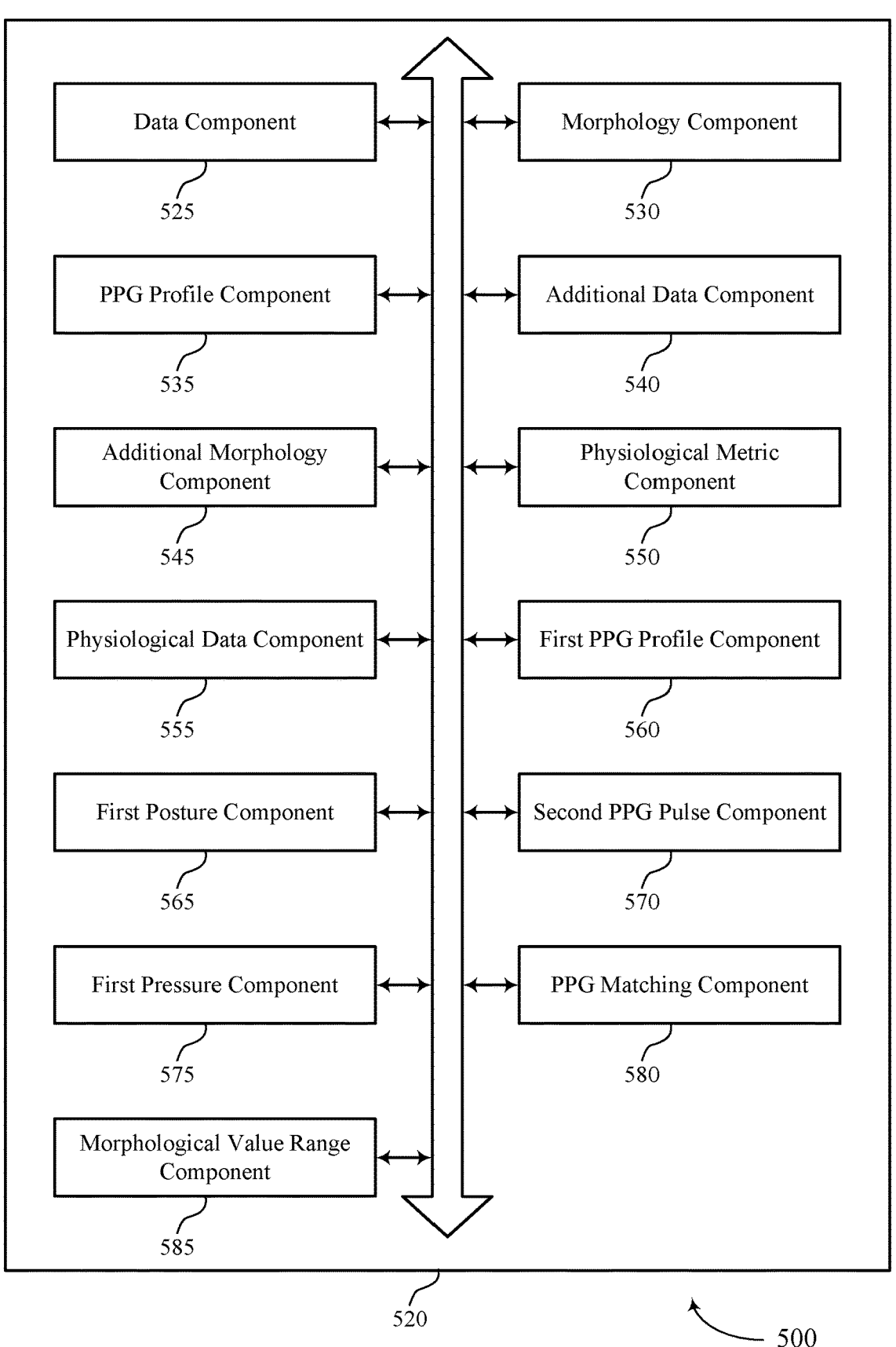
FIG. 5 illustrates a block diagram of a wearable application that supports techniques for identifying representative PPG pulses in accordance with aspects of the present disclosure.

FIG. 5 illustrates a block diagram 500 of a wearable application 520 that supports techniques for identifying representative PPG pulses in accordance with aspects of the present disclosure. The wearable application 520 may be an example of aspects of a wearable application or a wearable application 420, or both, as described herein. The wearable application 520, or various components thereof, may be an example of means for performing various aspects of techniques for identifying representative PPG pulses as described herein. For example, the wearable application 520 may include a data component 525, a morphology component 530, a PPG profile component 535, an additional data component 540, an additional morphology component 545, a physiological metric component 550, a physiological data component 555, a first PPG profile component 560, a first posture component 565, a second PPG pulse component 570, a first pressure component 575, a PPG matching component 580, a morphological value range component 585, or any combination thereof. Each of these components may communicate, directly or indirectly, with one another (e.g., via one or more buses).

The data component 525 may be configured as or otherwise support a means for acquiring PPG data from a user via a wearable device, the PPG data comprising a first set of PPG pulses. The morphology component 530 may be configured as or otherwise support a means for comparing a plurality of morphological features of the plurality of PPG pulses based at least in part on acquiring the PPG data. The PPG profile component 535 may be configured as or otherwise support a means for determining one or more PPG profiles based at least in part on a comparison of the plurality of morphological features, wherein the one or more PPG profiles each comprise a plurality of morphological value ranges for the plurality of morphological features. The additional data component 540 may be configured as or otherwise support a means for acquiring additional PPG data from the user via the wearable device, the additional PPG data comprising a second set of PPG pulses. The additional morphology component 545 may be configured as or otherwise support a means for determining that one or more PPG pulses from the second set of PPG pulses match the one or more PPG profiles based at least in part on a plurality of morphological feature values of the one or more PPG pulses satisfying the plurality of morphological value ranges of the one or more PPG profiles. The physiological metric component 550 may be configured as or otherwise support a means for determining, using the one or more PPG pulses, one or more physiological metrics associated with the user based at least in part on the one or more PPG pulses matching the one or more PPG profiles.

In some examples, the data component 525 may be configured as or otherwise support a means for determining a first set of PPG profiles associated with the first wavelength. In some examples, the additional data component 540 may be configured as or otherwise support a means for determining a second set of PPG profiles associated with the second wavelength, wherein the one or more PPG profiles are included within the first set of PPG profiles, the second set of PPG profiles, or both, wherein determining the one or more PPG pulses match the one or more PPG profiles is based at least in part on determining the first set of PPG profiles, the second set of PPG profiles, or both.

In some examples, the physiological data component 555 may be configured as or otherwise support a means for acquiring physiological data from the user via the wearable device, the physiological data acquired during a first time interval that the user is in a first posture and a second time interval that the user is in a second posture. In some examples, the first PPG profile component 560 may be configured as or otherwise support a means for determining a first set of PPG profiles associated with the first posture and a second set of PPG profiles associated with the second posture based at least in part on the physiological data, wherein the first set of PPG profiles comprise the one or more PPG profiles. In some examples, the first posture component 565 may be configured as or otherwise support a means for determining that the user is in the first posture throughout a third time interval. In some examples, the second PPG pulse component 570 may be configured as or otherwise support a means for comparing the second set of PPG pulses acquired during the third time interval with the first set of PPG profiles based at least in part on determining that the user is in the first posture throughout the third time interval, wherein determining that the one or more PPG pulses match the one or more PPG profiles of the first set of PPG profiles is based at least in part on the comparison.

In some examples, the physiological data component 555 may be configured as or otherwise support a means for acquiring physiological data from the user via the wearable device, the physiological data acquired during a first time interval associated with a first pressure between the wearable device and a tissue of the user a second time interval associated with a second pressure between the wearable device and the tissue of the user. In some examples, the first PPG profile component 560 may be configured as or otherwise support a means for determining a first set of PPG profiles associated with the first pressure and a second set of PPG profiles associated with the second pressure based at least in part on the physiological data, wherein the first set of PPG profiles comprise the one or more PPG profiles. In some examples, the first pressure component 575 may be configured as or otherwise support a means for identifying that the wearable device is associated with the first pressure between the wearable device and the tissue throughout a third time interval. In some examples, the second PPG pulse component 570 may be configured as or otherwise support a means for comparing the second set of PPG pulses acquired during the third time interval with the first set of PPG profiles based at least in part on identifying the first pressure throughout the third time interval, wherein determining that the one or more PPG pulses match the one or more PPG profiles of the first set of PPG profiles is based at least in part on the comparison.

In some examples, identifying that the wearable device is associated with the first pressure throughout the third time interval based at least in part on additional physiological data acquired by the wearable device throughout the third time interval. In some examples, the additional physiological data comprises pressure data.

In some examples, to support determining the one or more PPG pulses match the one or more PPG profiles, the PPG matching component 580 may be configured as or otherwise support a means for determining that a plurality of consecutive PPG pulses match the one or more PPG profiles, wherein the one or more physiological metrics are based at least in part on the plurality of consecutive PPG pulses.

In some examples, the morphological value range component 585 may be configured as or otherwise support a means for determining the plurality of morphological value ranges for the plurality of morphological features based at least in part on the comparison.

In some examples, the plurality of morphological value ranges comprise a range of average morphological values for each morphological feature, a range of median morphological values for each morphological feature, a range of mode morphological values for each morphological feature, or any combination theorem.

In some examples, the plurality of morphological features comprise an amplitude of the first set of PPG pulses, a duration of the first set of PPG pulses, a slope of the first set of PPG pulses, a curvature of the first set of PPG pulses, a relationship between peaks of the first set of PPG pulses, or any combination thereof.

In some examples, the one or more physiological metrics comprise a heart rate metric, an HRV metric, a blood oxygen saturation metric, a blood pressure metric, an arterial reactivity metric, or any combination thereof.

In some examples, the wearable device comprises a wearable ring device.

In some examples, the wearable device is configured to acquire the PPG data, the additional PPG data, or both, based at least in part on arterial blood flow of the user.

Figure 6:
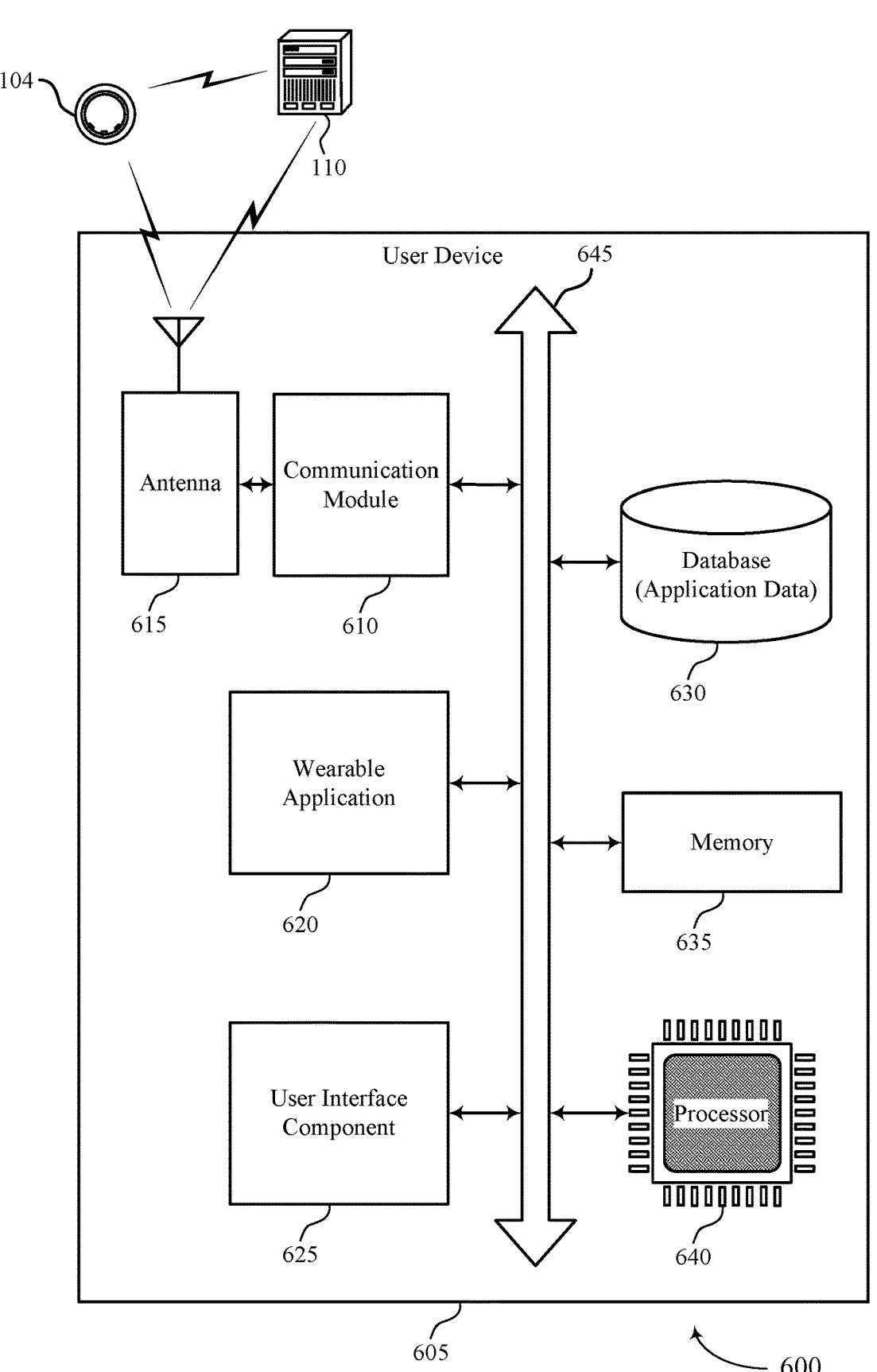
FIG. 6 illustrates a diagram of a system including a device that supports techniques for identifying representative PPG pulses in accordance with aspects of the present disclosure.

FIG. 6 illustrates a diagram of a system 600 including a device 605 that supports techniques for identifying representative PPG pulses in accordance with aspects of the present disclosure. The device 605 may be an example of or include the components of a device 405 as described herein. The device 605 may include an example of a user device 106, as described previously herein. The device 605 may include components for bi-directional communications including components for transmitting and receiving communications with a wearable device 104 and a server 110, such as a wearable application 620, a communication module 610, an antenna 615, a user interface component 625, a database (application data) 630, a memory 635, and a processor 640. These components may be in electronic communication or otherwise coupled (e.g., operatively, communicatively, functionally, electronically, electrically) via one or more buses (e.g., a bus 645).

The communication module 610 may manage input and output signals for the device 605 via the antenna 615. The communication module 610 may include an example of the communication module 220-*b* of the user device 106 shown and described in FIG. 2. In this regard, the communication module 610 may manage communications with the ring 104 and the server 110, as illustrated in FIG. 2. The communication module 610 may also manage peripherals not integrated into the device 605. In some cases, the communication module 610 may represent a physical connection or port to an external peripheral. In some cases, the communication module 610 may utilize an operating system such as iOS®, ANDROID®, MS-DOS®, MS-WINDOWS®, OS/2®, UNIX®, LINUX®, or another known operating system. In other cases, the communication module 610 may represent or interact with a wearable device (e.g., ring 104), modem, a keyboard, a mouse, a touchscreen, or a similar device. In some cases, the communication module 610 may be implemented as part of the processor 640. In some examples, a user may interact with the device 605 via the communication module 610, user interface component 625, or via hardware components controlled by the communication module 610.

In some cases, the device 605 may include a single antenna 615. However, in some other cases, the device 605 may have more than one antenna 615, which may be capable of concurrently transmitting or receiving multiple wireless transmissions. The communication module 610 may communicate bi-directionally, via the one or more antennas 615, wired, or wireless links as described herein. For example, the communication module 610 may represent a wireless transceiver and may communicate bi-directionally with another wireless transceiver. The communication module 610 may also include a modem to modulate the packets, to provide the modulated packets to one or more antennas 615 for transmission, and to demodulate packets received from the one or more antennas 615.

The user interface component 625 may manage data storage and processing in a database 630. In some cases, a user may interact with the user interface component 625. In other cases, the user interface component 625 may operate automatically without user interaction. The database 630 may be an example of a single database, a distributed database, multiple distributed databases, a data store, a data lake, or an emergency backup database.

The memory 635 may include RAM and ROM. The memory 635 may store computer-readable, computer-executable software including instructions that, when executed, cause the processor 640 to perform various functions described herein. In some cases, the memory 635 may contain, among other things, a BIOS which may control basic hardware or software operation such as the interaction with peripheral components or devices.

The processor 640 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 640 may be configured to operate a memory array using a memory controller. In other cases, a memory controller may be integrated into the processor 640. The processor 640 may be configured to execute computer-readable instructions stored in a memory 635 to perform various functions (e.g., functions or tasks supporting a method and system for sleep staging algorithms).

For example, the wearable application 620 may be configured as or otherwise support a means for acquiring PPG data from a user via a wearable device, the PPG data comprising a first set of PPG pulses. The wearable application 620 may be configured as or otherwise support a means for comparing a plurality of morphological features of the plurality of PPG pulses based at least in part on acquiring the PPG data. The wearable application 620 may be configured as or otherwise support a means for determining one or more PPG profiles based at least in part on a comparison of the plurality of morphological features, wherein the one or more PPG profiles each comprise a plurality of morphological value ranges for the plurality of morphological features. The wearable application 620 may be configured as or otherwise support a means for acquiring additional PPG data from the user via the wearable device, the additional PPG data comprising a second set of PPG pulses. The wearable application 620 may be configured as or otherwise support a means for determining that one or more PPG pulses from the second set of PPG pulses match the one or more PPG profiles based at least in part on a plurality of morphological feature values of the one or more PPG pulses satisfying the plurality of morphological value ranges of the one or more PPG profiles. The wearable application 620 may be configured as or otherwise support a means for determining, using the one or more PPG pulses, one or more physiological metrics associated with the user based at least in part on the one or more PPG pulses matching the one or more PPG profiles.

By including or configuring the wearable application 620 in accordance with examples as described herein, the device 605 may support techniques for improved accuracy of physiological measurements. In some examples, the device 605 may support techniques to determine which PPG pulses may be used to perform measurements. As such, these techniques may collect multiple PPG pulses and determine one or more representative PPG pulses that accurately represent the physiological metrics of the user. Alternatively, the device 605 may support techniques to remove one or more PPG pulses that fail to reflect accurate physiological metrics of the user.

The wearable application 620 may include an application (e.g., "app"), program, software, or other component which is configured to facilitate communications with a ring 104, server 110, other user devices 106, and the like. For example, the wearable application 620 may include an application executable on a user device 106 which is configured to receive data (e.g., physiological data) from a ring 104, perform processing operations on the received data, transmit and receive data with the servers 110, and cause presentation of data to a user 102.

FIG. 7 illustrates a flowchart showing a method 700 that supports techniques for identifying representative PPG pulses in accordance with aspects of the present disclosure. The operations of the method 700 may be implemented by a user device or its components as described herein. For example, the operations of the method 700 may be performed by a user device as described with reference to FIGS. 1 through 6. In some examples, a user device may execute a set of instructions to control the functional elements of the user device to perform the described functions. Additionally, or alternatively, the user device may perform aspects of the described functions using special-purpose hardware.

At 705, the method may include acquiring PPG data from a user via a wearable device, the PPG data comprising a first set of PPG pulses. The operations of 705 may be performed in accordance with examples as disclosed herein. In some examples, aspects of the operations of 705 may be performed by a data component 525 as described with reference to FIG. 5.

At 710, the method may include comparing a plurality of morphological features of the plurality of PPG pulses based at least in part on acquiring the PPG data. The operations of 710 may be performed in accordance with examples as disclosed herein. In some examples, aspects of the operations of 710 may be performed by a morphology component 530 as described with reference to FIG. 5.

At 715, the method may include determining one or more PPG profiles based at least in part on a comparison of the plurality of morphological features, where the one or more PPG profiles each comprise a plurality of morphological value ranges for the plurality of morphological features. The operations of 715 may be performed in accordance with examples as disclosed herein. In some examples, aspects of the operations of 715 may be performed by a PPG profile component 535 as described with reference to FIG. 5.

At 720, the method may include acquiring additional PPG data from the user via the wearable device, the additional PPG data comprising a second set of PPG pulses. The operations of 720 may be performed in accordance with examples as disclosed herein. In some examples, aspects of the operations of 720 may be performed by an additional data component 540 as described with reference to FIG. 5.

At 725, the method may include determining that one or more PPG pulses from the second set of PPG pulses match the one or more PPG profiles based at least in part on a plurality of morphological feature values of the one or more PPG pulses satisfying the plurality of morphological value ranges of the one or more PPG profiles. The operations of 725 may be performed in accordance with examples as disclosed herein. In some examples, aspects of the operations of 725 may be performed by an additional morphology component 545 as described with reference to FIG. 5.

At 730, the method may include determining, using the one or more PPG pulses, one or more physiological metrics associated with the user based at least in part on the one or more PPG pulses matching the one or more PPG profiles. The operations of 730 may be performed in accordance with examples as disclosed herein. In some examples, aspects of the operations of 730 may be performed by a physiological metric component 550 as described with reference to FIG. 5.

FIG. 8 illustrates a flowchart showing a method 800 that supports techniques for identifying representative PPG pulses in accordance with aspects of the present disclosure. The operations of the method 800 may be implemented by a user device or its components as described herein. For example, the operations of the method 800 may be performed by a user device as described with reference to FIGS. 1 through 6. In some examples, a user device may execute a set of instructions to control the functional elements of the user device to perform the described functions. Additionally, or alternatively, the user device may perform aspects of the described functions using special-purpose hardware.

At 805, the method may include acquiring PPG data from a user via a wearable device, the PPG data comprising a first set of PPG pulses. The operations of 805 may be performed in accordance with examples as disclosed herein. In some examples, aspects of the operations of 805 may be performed by a data component 525 as described with reference to FIG. 5.

At 810, the method may include comparing a plurality of morphological features of the plurality of PPG pulses based at least in part on acquiring the PPG data. The operations of 810 may be performed in accordance with examples as disclosed herein. In some examples, aspects of the operations of 810 may be performed by a morphology component 530 as described with reference to FIG. 5.

At 815, the method may include determining one or more PPG profiles based at least in part on a comparison of the plurality of morphological features, where the one or more PPG profiles each comprise a plurality of morphological value ranges for the plurality of morphological features. The operations of 815 may be performed in accordance with examples as disclosed herein. In some examples, aspects of the operations of 815 may be performed by a PPG profile component 535 as described with reference to FIG. 5.

At 820, the method may include determining a first set of PPG profiles associated with the first wavelength. The operations of 820 may be performed in accordance with examples as disclosed herein. In some examples, aspects of the operations of 820 may be performed by a data component 525 as described with reference to FIG. 5.

At 825, the method may include determining a second set of PPG profiles associated with the second wavelength, where the one or more PPG profiles are included within the first set of PPG profiles, the second set of PPG profiles, or both. The operations of 825 may be performed in accordance with examples as disclosed herein. In some examples, aspects of the operations of 825 may be performed by an additional data component 540 as described with reference to FIG. 5.

At 830, the method may include acquiring additional PPG data from the user via the wearable device, the additional PPG data comprising a second set of PPG pulses. The operations of 830 may be performed in accordance with examples as disclosed herein. In some examples, aspects of the operations of 830 may be performed by an additional data component 540 as described with reference to FIG. 5.

At 835, the method may include determining that one or more PPG pulses from the second set of PPG pulses match the one or more PPG profiles based at least in part on a plurality of morphological feature values of the one or more PPG pulses satisfying the plurality of morphological value ranges of the one or more PPG profiles, where determining the one or more PPG pulses match the one or more PPG profiles is based at least in part on determining the first set of PPG profiles, the second set of PPG profiles, or both. The operations of 835 may be performed in accordance with examples as disclosed herein. In some examples, aspects of the operations of 835 may be performed by an additional morphology component 545 as described with reference to FIG. 5.

At 840, the method may include determining, using the one or more PPG pulses, one or more physiological metrics associated with the user based at least in part on the one or more PPG pulses matching the one or more PPG profiles. The operations of 840 may be performed in accordance with examples as disclosed herein. In some examples, aspects of the operations of 840 may be performed by a physiological metric component 550 as described with reference to FIG. 5.

It should be noted that the methods described above describe possible implementations, and that the operations and the steps may be rearranged or otherwise modified and that other implementations are possible. Furthermore, aspects from two or more of the methods may be combined.

A method is described. The method may include acquiring PPG data from a user via a wearable device, the PPG data comprising a first set of PPG pulses, comparing a plurality of morphological features of the plurality of PPG pulses based at least in part on acquiring the PPG data, determining one or more PPG profiles based at least in part on a comparison of the plurality of morphological features, wherein the one or more PPG profiles each comprise a plurality of morphological value ranges for the plurality of morphological features, acquiring additional PPG data from the user via the wearable device, the additional PPG data comprising a second set of PPG pulses, determining that one or more PPG pulses from the second set of PPG pulses match the one or more PPG profiles based at least in part on a plurality of morphological feature values of the one or more PPG pulses satisfying the plurality of morphological value ranges of the one or more PPG profiles, and determining, using the one or more PPG pulses, one or more physiological metrics associated with the user based at least in part on the one or more PPG pulses matching the one or more PPG profiles.

An apparatus is described. The apparatus may include a processor, memory coupled with the processor, and instructions stored in the memory. The instructions may be executable by the processor to cause the apparatus to acquire PPG data from a user via a wearable device, the PPG data comprising a first set of PPG pulses, compare a plurality of morphological features of the plurality of PPG pulses based at least in part on acquiring the PPG data, determine one or more PPG profiles based at least in part on a comparison of the plurality of morphological features, wherein the one or more PPG profiles each comprise a plurality of morphological value ranges for the plurality of morphological features, acquire additional PPG data from the user via the wearable device, the additional PPG data comprising a second set of PPG pulses, determine that one or more PPG pulses from the second set of PPG pulses match the one or more PPG profiles based at least in part on a plurality of morphological feature values of the one or more PPG pulses satisfying the plurality of morphological value ranges of the one or more PPG profiles, and determine, using the one or more PPG pulses, one or more physiological metrics associated with the user based at least in part on the one or more PPG pulses matching the one or more PPG profiles.

Another apparatus is described. The apparatus may include means for acquiring PPG data from a user via a wearable device, the PPG data comprising a first set of PPG pulses, means for comparing a plurality of morphological features of the plurality of PPG pulses based at least in part on acquiring the PPG data, means for determining one or more PPG profiles based at least in part on a comparison of the plurality of morphological features, wherein the one or more PPG profiles each comprise a plurality of morphological value ranges for the plurality of morphological features, means for acquiring additional PPG data from the user via the wearable device, the additional PPG data comprising a second set of PPG pulses, means for determining that one or more PPG pulses from the second set of PPG pulses match the one or more PPG profiles based at least in part on a plurality of morphological feature values of the one or more PPG pulses satisfying the plurality of morphological value ranges of the one or more PPG profiles, and means for determining, using the one or more PPG pulses, one or more physiological metrics associated with the user based at least in part on the one or more PPG pulses matching the one or more PPG profiles.

A non-transitory computer-readable medium storing code is described. The code may include instructions executable by a processor to acquire PPG data from a user via a wearable device, the PPG data comprising a first set of PPG pulses, compare a plurality of morphological features of the plurality of PPG pulses based at least in part on acquiring the PPG data, determine one or more PPG profiles based at least in part on a comparison of the plurality of morphological features, wherein the one or more PPG profiles each comprise a plurality of morphological value ranges for the plurality of morphological features, acquire additional PPG data from the user via the wearable device, the additional PPG data comprising a second set of PPG pulses, determine that one or more PPG pulses from the second set of PPG pulses match the one or more PPG profiles based at least in part on a plurality of morphological feature values of the one or more PPG pulses satisfying the plurality of morphological value ranges of the one or more PPG profiles, and determine, using the one or more PPG pulses, one or more physiological metrics associated with the user based at least in part on the one or more PPG pulses matching the one or more PPG profiles.

Some examples of the method, apparatuses, and non-transitory computer-readable medium described herein may further include operations, features, means, or instructions for determining a first set of PPG profiles associated with the first wavelength and determining a second set of PPG profiles associated with the second wavelength, wherein the one or more PPG profiles may be included within the first set of PPG profiles, the second set of PPG profiles, or both, wherein determining the one or more PPG pulses match the one or more PPG profiles may be based at least in part on determining the first set of PPG profiles, the second set of PPG profiles, or both.

Some examples of the method, apparatuses, and non-transitory computer-readable medium described herein may further include operations, features, means, or instructions for acquiring physiological data from the user via the wearable device, the physiological data acquired during a first time interval that the user may be in a first posture and a second time interval that the user may be in a second posture, determining a first set of PPG profiles associated with the first posture and a second set of PPG profiles associated with the second posture based at least in part on the physiological data, wherein the first set of PPG profiles comprise the one or more PPG profiles, determining that the user may be in the first posture throughout a third time interval, and comparing the second set of PPG pulses acquired during the third time interval with the first set of PPG profiles based at least in part on determining that the user may be in the first posture throughout the third time interval, wherein determining that the one or more PPG pulses match the one or more PPG profiles of the first set of PPG profiles may be based at least in part on the comparison.

Some examples of the method, apparatuses, and non-transitory computer-readable medium described herein may further include operations, features, means, or instructions for acquiring physiological data from the user via the wearable device, the physiological data acquired during a first time interval associated with a first pressure between the wearable device and a tissue of the user a second time interval associated with a second pressure between the wearable device and the tissue of the user, determining a first set of PPG profiles associated with the first pressure and a second set of PPG profiles associated with the second pressure based at least in part on the physiological data, wherein the first set of PPG profiles comprise the one or more PPG profiles, identifying that the wearable device may be associated with the first pressure between the wearable device and the tissue throughout a third time interval, and comparing the second set of PPG pulses acquired during the third time interval with the first set of PPG profiles based at least in part on identifying the first pressure throughout the third time interval, wherein determining that the one or more PPG pulses match the one or more PPG profiles of the first set of PPG profiles may be based at least in part on the comparison.

Some examples of the method, apparatuses, and non-transitory computer-readable medium described herein may further include operations, features, means, or instructions for identifying that the wearable device may be associated with the first pressure throughout the third time interval based at least in part on additional physiological data acquired by the wearable device throughout the third time interval and the additional physiological data comprises pressure data.

In some examples of the method, apparatuses, and non-transitory computer-readable medium described herein, determining the one or more PPG pulses match the one or more PPG profiles may include operations, features, means, or instructions for determining that a plurality of consecutive PPG pulses match the one or more PPG profiles, wherein the one or more physiological metrics may be based at least in part on the plurality of consecutive PPG pulses.

Some examples of the method, apparatuses, and non-transitory computer-readable medium described herein may further include operations, features, means, or instructions for determining the plurality of morphological value ranges for the plurality of morphological features based at least in part on the comparison.

In some examples of the method, apparatuses, and non-transitory computer-readable medium described herein, the plurality of morphological value ranges comprise a range of average morphological values for each morphological feature, a range of median morphological values for each morphological feature, a range of mode morphological values for each morphological feature, or any combination theorem.

In some examples of the method, apparatuses, and non-transitory computer-readable medium described herein, the plurality of morphological features comprise an amplitude of the first set of PPG pulses, a duration of the first set of PPG pulses, a slope of the first set of PPG pulses, a curvature of the first set of PPG pulses, a relationship between peaks of the first set of PPG pulses, or any combination thereof.

In some examples of the method, apparatuses, and non-transitory computer-readable medium described herein, the one or more physiological metrics comprise a heart rate metric, an HRV metric, a blood oxygen saturation metric, a blood pressure metric, an arterial reactivity metric, or any combination thereof.

In some examples of the method, apparatuses, and non-transitory computer-readable medium described herein, the wearable device comprises a wearable ring device.

In some examples of the method, apparatuses, and non-transitory computer-readable medium described herein, the wearable device may be configured to acquire the PPG data, the additional PPG data, or both, based at least in part on arterial blood flow of the user.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method comprising:

acquiring photoplethysmogram (PPG) data from a user via a wearable device using first light associated with a first wavelength and second light associated with a second wavelength, the PPG data comprising a first set of PPG pulses;

comparing, across the first set of PPG pulses, a plurality of morphological features of each PPG pulse of the first set of PPG pulses based at least in part on acquiring the PPG data;

determining a first set of PPG profiles associated with the first wavelength that are representative of the PPG data acquired from the user using the first light based at least in part on a comparison of the plurality of morphological features of each PPG pulse of the first set of PPG pulses associated with the first wavelength, wherein each profile of the first set of PPG profiles comprises a plurality of morphological value ranges for the plurality of morphological features based at least in part on morphological values of each PPG pulse of the first set of PPG pulses associated with the first wavelength;

determining a second set of PPG profiles associated with the second wavelength that are representative of the PPG data acquired from the user using the second light based at least in part on a comparison of the plurality of morphological features of each PPG pulse of the first set of PPG pulses associated with the second wavelength, wherein each profile of the second set of PPG profiles comprises a plurality of morphological value ranges for the plurality of morphological features based at least in part on morphological values of each PPG pulse of the first set of PPG pulses associated with the second wavelength;

determining one or more PPG profiles that are representative of the PPG data acquired from the user based at least in part on determining the first set of PPG profiles, the second set of PPG profiles, or both, wherein the one or more PPG profiles are included within the first set of PPG profiles, the second set of PPG profiles, or both;

acquiring additional PPG data from the user via the wearable device, the additional PPG data comprising a second set of PPG pulses;

determining that one or more PPG pulses from the second set of PPG pulses match the one or more PPG profiles based at least in part on a plurality of morphological feature values of the one or more PPG pulses satisfying the plurality of morphological value ranges of the one or more PPG profiles; and determining, using the one or more PPG pulses, one or more physiological metrics associated with the user based at least in part on the one or more PPG pulses matching the one or more PPG profiles and refraining from using one or more additional PPG pulses of the second set of PPG pulses that do not match the one or more PPG profiles.

2. The method of claim 1, further comprising:

acquiring physiological data from the user via the wearable device, the physiological data acquired during a first time interval that the user is in a first posture and a second time interval that the user is in a second posture;

determining a third set of PPG profiles associated with the first posture and a fourth set of PPG profiles associated with the second posture based at least in part on the physiological data, wherein the third set of PPG profiles comprise the one or more PPG profiles;

determining that the user is in the first posture throughout a third time interval; and comparing the second set of PPG pulses acquired during the third time interval with the third set of PPG profiles based at least in part on determining that the user is in the first posture throughout the third time interval, wherein determining that the one or more PPG pulses match the one or more PPG profiles of the third set of PPG profiles is based at least in part on the comparison.

3. The method of claim 1, further comprising:

acquiring physiological data from the user via the wearable device, the physiological data acquired during a first time interval associated with a first pressure between the wearable device and a tissue of the user during a second time interval associated with a second pressure between the wearable device and the tissue of the user;

determining a third set of PPG profiles associated with the first pressure and a fourth set of PPG profiles associated with the second pressure based at least in part on the physiological data, wherein the third set of PPG profiles comprise the one or more PPG profiles;

identifying that the wearable device is associated with the first pressure between the wearable device and the tissue throughout a third time interval; and comparing the second set of PPG pulses acquired during the third time interval with the third set of PPG profiles based at least in part on identifying the first pressure throughout the third time interval, wherein determining that the one or more PPG pulses match the one or more PPG profiles of the third set of PPG profiles is based at least in part on the comparison.

4. The method of claim 3, wherein identifying that the wearable device is associated with the first pressure throughout the third time interval based at least in part on additional physiological data acquired by the wearable device throughout the third time interval, and wherein the additional physiological data comprises pressure data.

5. The method of claim 1, wherein determining the one or more PPG pulses match the one or more PPG profiles comprises:

determining that a plurality of consecutive PPG pulses match the one or more PPG profiles, wherein the one or more physiological metrics are based at least in part on the plurality of consecutive PPG pulses.

6. The method of claim 1, further comprising:

determining the plurality of morphological value ranges for the plurality of morphological features based at least in part on the comparison.

7. The method of claim 6, wherein the plurality of morphological value ranges comprise a range of average morphological values for each morphological feature, a range of median morphological values for each morphological feature, a range of mode morphological values for each morphological feature, or any combination thereof.

8. The method of claim 1, wherein the plurality of morphological features comprise an amplitude of the first set of PPG pulses, a duration of the first set of PPG pulses, a slope of the first set of PPG pulses, a curvature of the first set of PPG pulses, a relationship between peaks of the first set of PPG pulses, or any combination thereof.

9. The method of claim 1, wherein the one or more physiological metrics comprise a heart rate metric, a heart rate variability metric, a blood oxygen saturation metric, a blood pressure metric, an arterial reactivity metric, or any combination thereof.

10. The method of claim 1, wherein the wearable device comprises a wearable ring device.

11. The method of claim 1, wherein the wearable device is configured to acquire the PPG data, the additional PPG data, or both, based at least in part on arterial blood flow of the user.

12. An apparatus, comprising:

a processor;

memory coupled with the processor; and instructions stored in the memory and executable by the processor to cause the apparatus to:

acquire photoplethysmogram (PPG) data from a user via a wearable device using first light associated with a first wavelength and second light associated with a second wavelength, the PPG data comprising a first set of PPG pulses;

compare, across the first set of PPG pulses, a plurality of morphological features of each PPG pulse of the first set of PPG pulses based at least in part on acquiring the PPG data;

determine a first set of PPG profiles associated with the first wavelength that are representative of the PPG data acquired from the user using the first light based at least in part on a comparison of the plurality of morphological features of each PPG pulse of the first set of PPG pulses associated with the first wavelength, wherein each profile of the first set of PPG profiles comprises a plurality of morphological value ranges for the plurality of morphological features based at least in part on morphological values of each PPG pulse of the first set of PPG pulses associated with the first wavelength;

determine a second set of PPG profiles associated with the second wavelength that are representative of the PPG data acquired from the user using the second light based at least in part on a comparison of the plurality of morphological features of each PPG pulse of the first set of PPG pulses associated with the second wavelength, wherein each profile of the second set of PPG profiles comprises a plurality of morphological value ranges for the plurality of morphological features based at least in part on morphological values of each PPG pulse of the first set of PPG pulses associated with the second wavelength;

determine one or more PPG profiles that are representative of the PPG data acquired from the user based at least in part on determining the first set of PPG profiles, the second set of PPG profiles, or both, wherein the one or more PPG profiles are included within the first set of PPG profiles, the second set of PPG profiles, or both;

acquire additional PPG data from the user via the wearable device, the additional PPG data comprising a second set of PPG pulses;

determine that one or more PPG pulses from the second set of PPG pulses match the one or more PPG profiles based at least in part on a plurality of morphological feature values of the one or more PPG pulses satisfying the plurality of morphological value ranges of the one or more PPG profiles; and determine, using the one or more PPG pulses, one or more physiological metrics associated with the user based at least in part on the one or more PPG pulses matching the one or more PPG profiles and refrain from using one or more additional PPG pulses of the second set of PPG pulses that do not match the one or more PPG profiles.

13. The apparatus of claim 12, wherein the instructions are further executable by the processor to cause the apparatus to:

acquire physiological data from the user via the wearable device, the physiological data acquired during a first time interval that the user is in a first posture and a second time interval that the user is in a second posture;

determine a third set of PPG profiles associated with the first posture and a fourth set of PPG profiles associated with the second posture based at least in part on the physiological data, wherein the third set of PPG profiles comprise the one or more PPG profiles;

determine that the user is in the first posture throughout a third time interval; and compare the second set of PPG pulses acquired during the third time interval with the third set of PPG profiles based at least in part on determining that the user is in the first posture throughout the third time interval, wherein determining that the one or more PPG pulses match the one or more PPG profiles of the third set of PPG profiles is based at least in part on the comparison.

14. The apparatus of claim 12, wherein the instructions are further executable by the processor to cause the apparatus to:

acquire physiological data from the user via the wearable device, the physiological data acquired during a first time interval associated with a first pressure between the wearable device and a tissue of the user a second time interval associated with a second pressure between the wearable device and the tissue of the user;

determine a third set of PPG profiles associated with the first pressure and a fourth set of PPG profiles associated with the second pressure based at least in part on the physiological data, wherein the third set of PPG profiles comprise the one or more PPG profiles;

identify that the wearable device is associated with the first pressure between the wearable device and the tissue throughout a third time interval; and compare the second set of PPG pulses acquired during the third time interval with the third set of PPG profiles based at least in part on identifying the first pressure throughout the third time interval, wherein determining that the one or more PPG pulses match the one or more PPG profiles of the third set of PPG profiles is based at least in part on the comparison.

15. The apparatus of claim 14, wherein identifying that the wearable device is associated with the first pressure throughout the third time interval based at least in part on additional physiological data acquired by the wearable device throughout the third time interval, and wherein the additional physiological data comprises pressure data.

16. The apparatus of claim 12, wherein the instructions to determine the one or more PPG pulses match the one or more PPG profiles are executable by the processor to cause the apparatus to:

determine that a plurality of consecutive PPG pulses match the one or more PPG profiles, wherein the one or more physiological metrics are based at least in part on the plurality of consecutive PPG pulses.

17. The apparatus of claim 12, wherein the instructions are further executable by the processor to cause the apparatus to:

determine the plurality of morphological value ranges for the plurality of morphological features based at least in part on the comparison.

18. A non-transitory computer-readable medium storing code, the code comprising instructions executable by a processor to:

acquire photoplethysmogram (PPG) data from a user via a wearable device using first light associated with a first wavelength and second light associated with a second wavelength, the PPG data comprising a first set of PPG pulses;

compare, across the first set of PPG pulses, a plurality of morphological features of each PPG pulse of the first set of PPG pulses based at least in part on acquiring the PPG data;

determine a first set of PPG profiles associated with the first wavelength that are representative of the PPG data acquired from the user using the first light based at least in part on a comparison of the plurality of morphological features of each PPG pulse of the first set of PPG pulses associated with the first wavelength, wherein each profile of the first set of PPG profiles comprises a plurality of morphological value ranges for the plurality of morphological features based at least in part on morphological values of each PPG pulse of the first set of PPG pulses associated with the first wavelength;

determine a second set of PPG profiles associated with the second wavelength that are representative of the PPG data acquired from the user using the second light based at least in part on a comparison of the plurality of morphological features of each PPG pulse of the first set of PPG pulses associated with the second wavelength, wherein each profile of the second set of PPG profiles comprises a plurality of morphological value ranges for the plurality of morphological features based at least in part on morphological values of each PPG pulse of the first set of PPG pulses associated with the second wavelength;

determine one or more PPG profiles that are representative of the PPG data acquired from the user based at least in part on determining the first set of PPG profiles, the second set of PPG profiles, or both, wherein the one or more PPG profiles are included within the first set of PPG profiles, the second set of PPG profiles, or both;

acquire additional PPG data from the user via the wearable device, the additional PPG data comprising a second set of PPG pulses;

determine that one or more PPG pulses from the second set of PPG pulses match the one or more PPG profiles based at least in part on a plurality of morphological feature values of the one or more PPG pulses satisfying the plurality of morphological value ranges of the one or more PPG profiles; and determine, using the one or more PPG pulses, one or more physiological metrics associated with the user based at least in part on the one or more PPG pulses matching the one or more PPG profiles and refrain from using one or more additional PPG pulses of the second set of PPG pulses that do not match the one or more PPG profiles.

* * * * *